(12) United States Patent
Zemach et al.

(10) Patent No.: US 6,399,118 B1
(45) Date of Patent: Jun. 4, 2002

(54) PROCESS FOR STORING ENRICHED NEMATODES

(75) Inventors: Shalom Zemach, Kfar Yona; Amos Tandler; William Koven, both of Eilat, all of (IL)

(73) Assignees: Fish Biotech Ltd., Jerusalem (IL); Israel Oceanographic and Limnological Research Ltd., Haifa (IL)

(*) Notice: Subject to any disclaimer, the term of this patent is extended or adjusted under 35 U.S.C. 154(b) by 0 days.

(21) Appl. No.: 09/893,875

(22) Filed: Jun. 29, 2001

(51) Int. Cl.$^7$ .......................... A01K 67/033; A23K 1/18
(52) U.S. Cl. .......................... 426/2; 426/443; 426/601; 426/641; 426/650
(58) Field of Search .......................... 426/2, 443, 641, 426/601, 650

(56) References Cited

U.S. PATENT DOCUMENTS

| | | | |
|---|---|---|---|
| 5,052,427 A | 10/1991 | Bedding | 119/6.7 |
| 5,183,950 A | 2/1993 | Popiel et al. | 800/2 |

FOREIGN PATENT DOCUMENTS

WO  WO95/18527  7/1995

OTHER PUBLICATIONS

The effect of dietary arachidonic acid (20:4n–6) on growth, survival and resistance to handling stress in gilthead seabream (*Sparus aurata*) larvae. Koven et al, Aquaculture 193 (2001) 107–122.

Enrichment of Artemia with free methionine. Tonheim et al, Aquaculture 190 (2000) 223–235.

Desiccation survival of the entomopathogenic nematode Steinernema feltiae: induction of anhydrobiosis Solomon et al Nematology 1999 vol. 1(1) 61–68.

Desiccation survival of parasitic nematodes. Perry Parasitology (1999) 119, S19–S20.

Osmotic Survival of the Entomopathogenic Nematode Steinernema carpocapsae. Glazer et al. Biological control 18, 251–257 (2000).

The potential of liposomes as a nutrient supplement in first–feeding marine fish larvae. Koven et al. Aquaculture Nutrition 1999, 5; 251–256.

The importance of n–3 highly unsaturated fatty acids for growth in larval *Sparus aurata* and their effect on survival lipid composition and size distribution. Aquaculture 104, 91–104, 1992.

*Primary Examiner*—Chhaya D. Sayala
(74) *Attorney, Agent, or Firm*—Mark M. Friedman

(57) ABSTRACT

A process for preserving and storing nematodes having an increased feeding value for later use as needed in the feeding of aquaculture organisms. In this process, nematodes are enriched with an additive such as essential fatty acids, vaccines, hormones, immunostimulants, attractants, nutrients and pigments. Liposomes can serve as a medium for feeding the additives to the nematodes. The enriched nematodes are then desiccated by inducing a quiescent anhydrobiosis (dehydration) and stored for off-the-shelf use as needed. When required for feeding, the desiccated enriched nematodes are rehydrated and fed to the aquaculture organisms.

17 Claims, 1 Drawing Sheet

PROCESS FOR STORING ENRICHED NEMATODES

FIELD AND BACKGROUND OF THE INVENTION

The present invention relates to aquaculture and, more particularly, to a method for "off-the-shelf" storage of enriched nematodes used in feeding aquaculture organisms such as fish and shrimp larvae.

A major bottleneck to the successful growing of marine fish with commercial potential is the rearing of the early developmental stages or larvae. During this time, mortality can range from about 60–100%, frequently due to insufficient or poor nutrition. For instance, hatcheries depend on the provision of live food or zooplankton to the larvae such as rotifers (*Brachionus plicatilis* or other Brachianus sp.) and brine shrimp (Artemia sp.). These zooplankters do not represent the natural diet but are relatively easy to grow in large quantities and are readily accepted by the larvae. On the other hand, the culture of these zooplankters requires a considerable investment in infrastructure (tanks, water and air pumps, water treatment) as well as energy and manpower. Moreover, the live food cannot be stored or is deficient in specific long chain polyunsaturated fatty acids (PUFA), such as docosahexaenoic acid (DHA) and eicosapentaenoic acid (EPA) which are necessary in the diet for rapidly growing larvae which can demonstrate daily a relative growth rate (RGR) of 25–50% (Koven, W., Tandler, A., Kissil, G. Wm., Sklan, D. 1992 The Importance of n-3 highly unsaturated fatty acids for growth in larval *Sparus aurata* and their effect on survival, lipid composition and size distribution. Aquaculture 104, 91–104). This is also true with arachidonic acid (ArA) which has recently been recognized as playing a central role in increasing stress resistance (Koven, W., Barr, Y., Lutzky, S., Ben-Atia. I., Weiss, R., Harel, M., Behrens, P., Tandler, A. 2001. The effect of arachidonic acid (20:4n–6) on growth, survival and resistance to handling stress in gilthead seabream (*Sparus aurata*) larvae. Aquaculture 193, 107–122). Consequently, rotifers and Artemia must be enriched with these PUFA, by feeding them commercial DHA and EPA preparations, before they are offered to the fish larvae.

Live food culture systems are frequently plagued by an inconsistent supply of zooplankters that have variable nutritional content and are susceptible to sudden population crashes. So for instance an interruption in the supply and/or an inconsistency in feed quality of food fed to the larvae can severely reduce their growth rate, extending the residence time in the hatchery or resulting in smaller, less robust larvae being transferred to the nursery, resulting in reduced growth and survival. In addition, poor feeding can cause stress, resulting in a decreased resistance to disease. In recent years, primarily due to over exploitation, there has been a rapid decline in the world wide availability of Artemia cysts resulting in fluctuating prices and reduced cyst quality compounding the problems of providing these zooplankters.

A clear advantage in the use of nematodes as a feed is in that the nematodes can be stored in a dormant-desiccated state, after enrichment. They can be encapsulated and revived at a later stage for feeding to larvae. This "off the shelf convenience" provides a dependable and nutritionally consistent food supply to the larvae that can be provided, with less investment, than other conventional live food species.

Essential fatty acids for marine larvae such as docosahexaenoic acid (22:6n–3), eicosapentaenoic acid (20:5n–3) and arachidonic acid (20:4n–6) can be provided to the nematodes through various oil emulsions. Previous studies have shown that nematodes readily filter the micelles of oil emulsions. Recent studies have shown that the use of liposomes to feed nematodes is a promising approach to widen the range of feeding additives that could be used for enrichment. Liposomes are small (0.025–1 μm) lipid vesicles consisting of an aqueous volume surrounded by a bi-lamellar phospholipid membrane. It is relatively easy to incorporate water-soluble vitamins, minerals, proteins and amino acids into the aqueous volume and/or lipid-soluble nutrients such as lipids, vitamins and pigments into the liposome's phospholipid membrane (Koven, W., Barr, Y., Hadas, E., Ben-Atia, I., Chen, Y., Weiss, R., Tandler, A. 1999. The potential of liposomes as a nutrient supplement in first-feeding marine fish larvae. Aquaculture Nutrition 5, 251–256).

A recent study showed that liposomes could be used to enrich *Artemia nauplii* with the free amino acid methionine (Tonheim, S.K., Koven, B, Rønnestad, I. 2000. Enrichment of Artemia with free methionine. Aquaculture 190, 223–235). This zooplankter is generally deficient in this amino acid and its enrichment may contribute to more efficient protein synthesis. This approach has recently been expanded to include the enrichment of nematodes with this and other free amino acids as well as free fatty acids, which stimulate digestive hormones in the larvae such as cholecystokinin (CCK). CCK is a major factor in the release of pancreatic enzymes resulting in enhanced digestion and assimilation of dietary nutrients. In addition, liposomes fed to nematodes containing immunostimulants, vaccines and other pharmaceuticals may stimulate disease and stress resistance in the larvae resulting in improved larval and juvenile fish quality.

U.S. Pat. No. 5,183,950 to Popiel et al teaches a method for commercial storage and shipment of entemogenous (parasitic to insects) nematodes. It relates to methods to desiccate, package, store, and ship insect parasitic nematodes in both large and small quantities while maintaining their viability and pathogenicity to insects. Popiel's method does not mention enriching the nematodes before storage.

U.S. Pat. No. 5,042,427 to Bedding describes a method of storing and transporting nematodes by using clay to dry the nematodes, which are revived when dispersed in water. Bedding's method does not mention enriching the nematodes before storage.

Desiccation of nematodes is also taught by Solomon et al. (Solomon A., Paperna I., Glazer I. 1999 Desiccation survival of the entomopathogenic nematode Steinernema feltiae: induction of anhydrobiosis Nematology 1 (1), 61–68) as well as by Perry (Perry R. 1999 Desiccation survival of parasitic nematodes. Parasitology 119,S19–S30). Here again there is no mention of enriching the nematodes before desiccation.

WWO Pat. No. 95/18527 to Agricultural Genetics Company LTD teaches enriching nematodes with various additives such as various oils and pigments for use as live feed for larvae. This method illustrates the advantages of feeding enriched nematodes to larvae but there is no mention of long term storage of the nematodes.

There is thus a widely recognized need for, and it would be highly advantageous to have, a process for preserving and storing nematodes having an increased feeding value devoid of the above limitations.

SUMMARY OF THE INVENTION

According to one aspect of the present invention there is provided a process for preserving nematodes having an increased feeding value. The process comprises the steps of enriching nematodes with aquaculture feed additives and desiccating enriched nematodes.

According to another aspect of the present invention there is provided an improved method of aquaculture. The method comprises the steps of enriching nematodes with aquaculture feed additives, desiccating enriched nematodes, storing the desiccated enriched nematodes, rehydrating and reviving the desiccated enriched nematodes; and feeding rehydrated enriched nematodes to an organism being grown in the aquaculture.

According to another aspect of the present invention there is provided an improved method of aquaculture. The method comprises the steps of desiccating nematodes, storing the desiccated nematodes, rehydrating and reviving the desiccated nematodes, enriching nematodes with aquaculture feed additives and feeding rehydrated enriched nematodes to an organism being grown in the aquaculture.

According to further features in preferred embodiments of the invention described below, the process further comprises the step of culturing nematodes.

According to still further features in the described preferred embodiments, the process further comprises the step of storing the desiccated nematodes.

According to still further features in the described preferred embodiments, the nematodes are free-living nematodes.

According to still further features in the described preferred embodiments, the free-living nematodes are of the species Panagrellus.

According to still further features in the described preferred embodiments, the step of enriching nematodes includes providing at least one enriching additive selected from the group consisting of essential fatty acids, vaccines, hormones, immunostimulants, attractants, nutrients and pigments.

According to still further features in the described preferred embodiments, the step of desiccating the nematodes is performed by inducing one item selected out of the group consisting of quiescent anhydrobiosis and osmobiosis.

According to still further features in the described preferred embodiments, the step of enriching is affected by feeding the nematodes with liposomes containing enriching additives.

Among the advantages of off-the shelf convenience are:
a) The ability to store enriched nematodes ensures constant food supply for the larvae. Due to the rapid daily larval growth rate (RGR of 25–50%), the interruption of food supply, as a result of equipment failure, crashes in rotifer and algal cultures and lower hatching rates in poor quality Artemia cysts, can translate into less than optimal larval growth and survival.
b) As batches of enriched nematodes can be tested for nutrient content before storage, consistent nutritional quality can be ensured before feeding larvae.
c) The ability to produce a product for storage, means that sufficient reserves can be built up. This is advantageous otherwise further investment in infrastructure, labor and energy as compared to any other traditional food supply method will be necessary.
d) The ability to store enriched nematodes is a basis for a commercial product that could compete with Artemia cysts, which is a resource plagued by dwindling supply, variable quality, occasional contamination with pesticides fluctuating high prices, and is a non-sustainable resource.
e) Newly hatched Artemia's body composition can reflect only natural processes in the environment in which the Artemia broodstock dwelled. Cyst laying, being a natural process, lends NO control over quality of the hatched nauplii, in terms of body composition. On the other hand nematodes, which address the same size larvae, can be enriched prior to their encapsulation for long term storage.

The present invention successfully addresses the shortcomings of the presently known configurations by providing a process for preserving and storing nematodes having an increased nutritional value for later use as needed in the feeding of aquaculture organisms.

BRIEF DESCRIPTION OF THE DRAWING

The invention is herein described, by way of example only, with reference to the accompanying drawing. With specific reference now to the drawing in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawing making apparent to those skilled in the art of how the several forms of the invention may be embodied in practice.

In the drawing.

DESCRIPTION OF THE PREFERRED EMBODIMENTS

Figure 1:
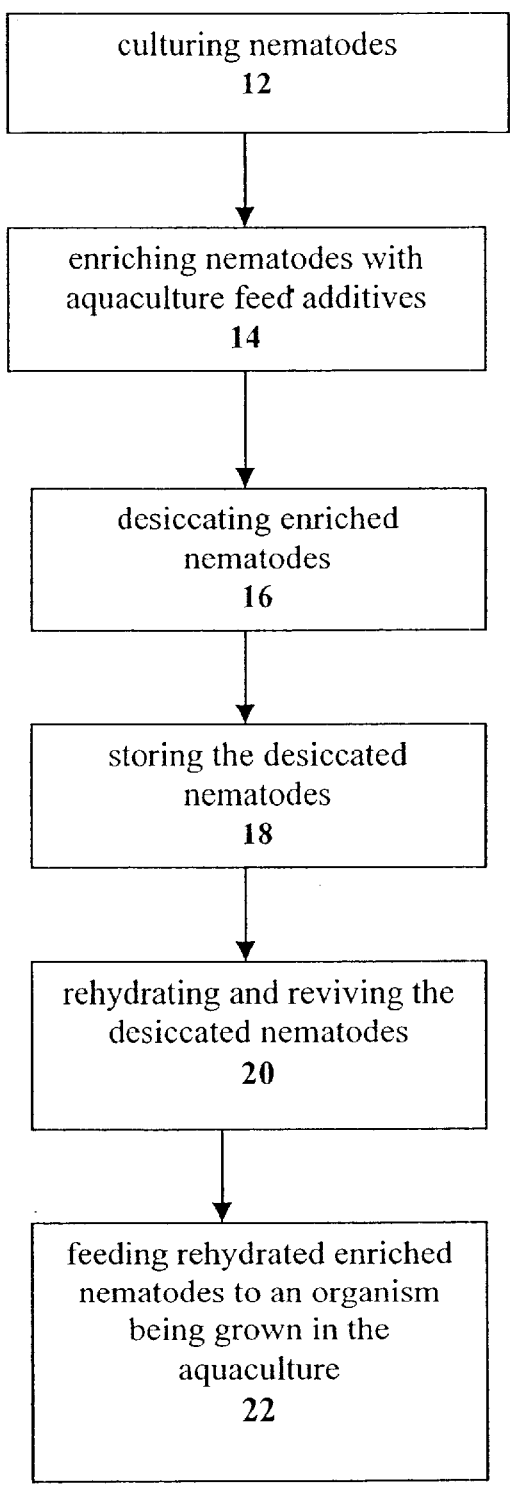
FIG. 1 is a flow chart of an improved method of aquaculture.

The present invention is of a method of aquaculture, which can be used for feeding larvae. Specifically, the present invention can be used to preserve and store enriched desiccated nematodes so that they may be taken "off the shelf", be rehydrated and revived for use as needed. This method omits the need for live aquaculture feed such as Artemia, rotifers, copepods etc.

The principles and operation of a method of aquaculture, according to the present invention, may be better understood with reference to the drawing and accompanying descriptions.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

For purposes of this specification and the accompanying claims, the term "nematode" refers to all types of nematodes. Although the methods of the present invention are practicable with all nematodes, they are preferably practiced with free-living (i.e. non-parasitic) nematodes, more preferably with the species Panagrellus.

For purposes of this specification and the accompanying claims, the term "desiccation" refers to removal of water from an organism by evaporation, by osmotic pressure or by any other means serving this purpose.

For purposes of this specification and the accompanying claims, the term "aquaculture" refers to the rearing and propagation of any aquatic organism.

For purposes of this specification and the accompanying claims, the term "enrich" refers to substances provided to nematodes via their diet, medium or otherwise, to increase the level of the respected substance in the nematode body prior to feeding it to the target organism and may include but are not restricted to essential fatty acids, vaccines, hormones, immunostimulants, attractants, nutrients or pigments.

Referring now to the drawing, FIG. 1 is a flow chart illustrating method 10 for preserving nematodes having an increased feeding value. Method 10 includes the step of culturing nematodes 12. Nematode culturing is known to those skilled in the art of nematology. Nematodes may be fed with yeasts and bacteria acting as mediators for delivering food to the nematodes. Alternately, or additionally, nematodes may be grown on an industrial scale with the use of fermentors.

According to method 10 of the present invention, nematodes are "enriched" with aquaculture feed additives 14 just prior to or alternately after harvest. The nematodes are enriched with at least one additive such as essential fatty acids, vaccines, hormones, immunostimulants, attractants, nutrients or pigments, which is added to the feed of the nematodes. A mediator that has been successfully used for feeding the additives to the nematodes is by penetrating the additives to liposomes and then feeding the liposomes to the nematodes. Essential fatty acids for marine larvae such as docosahexaenoic acid (22:6n–3), eicosapentaenoic acid (20:5n–3) and arachidonic acid (20:4n–6) can be provided to the nematodes through various oil emulsions. In addition liposomes, containing immunostimulants and vaccines, can be fed to nematodes, which may improve disease resistance in the larvae feeding on them. Moreover, nematodes can be fed liposomes containing specific free amino (FAA) and fatty acids (FFA) that stimulate digestive hormones in the larvae such as cholecystokinin (CCK). CCK is a major factor in the release of pancreatic enzymes resulting in enhanced digestion and assimilation of dietary nutrients. Other FAA can be incorporated in liposomes to stimulate appetite or to improve larval protein synthesis by giving a more balanced amino acid composition.

After feeding the nematodes with the enriching additive, the enriched nematodes are ready for feeding to the breeding larvae or are desiccated 16 for future "off-the-shelf" use. Several prior methods of desiccation are discussed above in the introduction and are known to those skilled in the art of nematology. A preferred method of desiccation is performed by inducing a quiescent anhydrobiosis or osmobiosis. Anhydrobiosis/osmobiosis or dehydration of the nematodes is optimally a quiescent anhydrobiosis. Quiescence is a spontaneous reversible response to unpredictable unfavorable environmental conditions and release from quiescence occurs when favorable conditions return. The desiccated and enriched nematodes are then stored 18 and are available in a dehydrated state for use as needed at a future date.

FIG. 1 further illustrates an improved method 10 of aquaculture. The method includes the step of culturing nematodes 12. Nematode culturing is known to those skilled in the art of nematology. Nematodes may be fed with yeasts and bacteria acting as mediators for delivering food to the nematodes. Alternately, or additionally, nematodes may be grown on an industrial scale with the use of fermentors.

According to method 10 of the present invention, after a period of time, before harvesting or alternately after harvesting, the nematodes are enriched with aquaculture feed additives 14. A novel means of incorporating feed additives into the nematodes is by using a mediator. A mediator which has been successfully used for feeding the feed additives to the nematodes are liposomes which contain feed additives. Alternately, or additionally, other mediators can be utilized for this purpose.

After feeding the nematodes with the enriching additive, the enriched nematodes are ready for feeding to the breeding larvae or are desiccated 16 for future use. Several prior methods of desiccation are discussed above in the introduction and are known to those skilled in the art of nematology. The desiccated enriched nematodes are then stored 18 and are available in a dehydrated state for off-the shelf use at a future date.

Before use, the desiccated enriched nematodes are rehydrated and revived 20. Following rehydration, the rehydrated enriched nematodes are fed to an organism being grown in aquaculture 22.

In an alternative embodiment of the present invention nematodes which have been cultured are desiccated and then stored. Prior to use the desiccated nematodes are rehydrated and revived and then the nematodes are enriched with feed additives and then fed to an organism being grown in the agriculture.

Although the invention has been described in conjunction with specific embodiments thereof, it is evident that many alternatives, modifications and variations will be apparent to those skilled in the art of nematology. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A process for preserving nematodes having an increased feeding value, for use in aquaculture, the process comprising the steps of:
    (a) enriching nematodes with aquaculture feed additives; and
    (b) desiccating enriched nematodes.

2. The process of claim 1, further comprising the step of:
    (c) culturing the nematodes.

3. The process of claim 1, further comprising the step of:
    (d) storing the desiccated enriched nematodes.

4. The process of claim 1, wherein the nematodes are free-living nematodes.

5. The process of claim 4, wherein said free-living nematodes are of the species Panagrellus.

6. The process of claim 1, wherein the step of enriching nematodes includes providing at least one enriching additive selected from the group consisting of essential fatty acids, vaccines, hormones, immunostimulants, attractants, nutrients and pigments.

7. The process of claim 1, wherein the step of desiccating the enriched nematodes is performed by inducing one item selected out of the group consisting of quiescent anhydrobiosis and osmobiosis.

8. The process of claim 1, wherein the step of enriching is affected by feeding the nematodes with liposomes containing enriching additives.

9. An improved method of aquaculture, the method comprising the steps of:
(a) enriching nematodes with aquaculture feed additives;
(b) desiccating enriched nematodes;
(c) storing desiccated enriched nematodes;
(d) rehydrating and reviving said desiccated enriched nematodes; and
(e) feeding rehydrated enriched nematodes to an organism being grown in the aquaculture.

10. The process of claim 9, wherein said nematodes are free-living nematodes.

11. The process of claim 9, wherein said free-living nematodes are of the species Panagrellus.

12. The process of claim 9, wherein the step of enriching nematodes includes at least providing one enriching additive selected from the group consisting of essential fatty acids, vaccines, hormones, immunostimulants, attractants, nutrients and pigments.

13. The process of claim 9, wherein the step of desiccating the enriched nematodes is performed by inducing one item selected out of the group consisting of quiescent anhydrobiosis and osmobiosis.

14. The process of claim 9, wherein the step of enriching is affected by feeding said nematodes with liposomes containing enriching additives.

15. An improved method of aquaculture, the method comprising the steps of:
(a) desiccating nematodes;
(b) storing said desiccated nematodes;
(c) rehydrating and reviving said desiccated nematodes;
(d) enriching nematodes with feed additives; and
(e) feeding rehydrated enriched nematodes to an organism being grown in the aquaculture.

16. The process of claim 15, wherein the step of enriching nematodes includes at least providing one enriching additive selected from the group consisting of essential fatty acids, vaccines, hormones, immunostimulants, attractants, nutrients and pigments.

17. The process of claim 15, wherein the step of desiccating the nematodes is performed by inducing one item selected out of the group consisting of quiescent anhydrobiosis and osmobiosis.

* * * * *